United States Patent [19]

Silvestrini

[11] 4,162,318
[45] Jul. 24, 1979

[54] USE OF TRAZODONE AND ETOPERIDONE IN PARKINSONISM AND IN OTHER EXTRAPYRAMIDAL SYNDROMES CHARACTERIZED BY TREMORS

[75] Inventor: Bruno Silvestrini, Rome, Italy

[73] Assignee: Aziende Chimiche Riunite Angelini Francesco A.C.R.A.F. S.p.A., Rome, Italy

[21] Appl. No.: 925,499

[22] Filed: Jul. 17, 1978

Related U.S. Application Data

[62] Division of Ser. No. 793,336, May 3, 1977, Pat. No. 4,132,791.

[30] Foreign Application Priority Data

May 5, 1976 [IT] Italy .................... 49321 A/76

[51] Int. Cl.² ........................................... A61K 31/495
[52] U.S. Cl. .................................................. 424/250
[58] Field of Search ........................................ 424/250

[56] References Cited

U.S. PATENT DOCUMENTS 3,381,009  4/1968  Polazzo et al. ............ 424/250
3,857,845  12/1974  Polazzo ..................... 424/250

Primary Examiner—Stanley J. Friedman

Attorney, Agent, or Firm—Ladas, Parry, Von Gehr, Goldsmith & Deschamps

[57] ABSTRACT

Treatment of tremors in Parkinsonism and in other extrapyramidal syndromes by administering an amount of trazodone of the formula

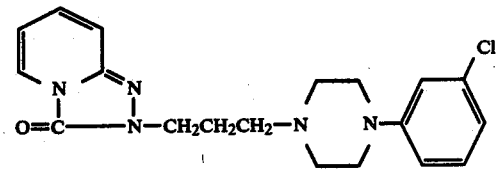

and or of etoperidone of the formula:

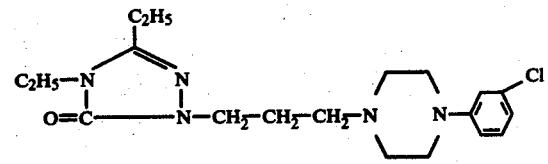

in the range of about 25 mg. to 100 mg. three times a day.

2 Claims, No Drawings

USE OF TRAZODONE AND ETOPERIDONE IN PARKINSONISM AND IN OTHER EXTRAPYRAMIDAL SYNDROMES CHARACTERIZED BY TREMORS

This is a division of application Ser. No. 793,336 filed May 3, 1977, now U.S. Pat. No. 4,132,791.

The present invention concerns the new application of two known drugs, compounds whose generic names used are respectively "trazodone" and "etoperidone". Etoperidone was formerly called "clopradone". Trazodone is 2-[3-[4-m-chlorophenyl)-1-piperazinyl]-propyl]-S-triazolo[4,3-2]-pyridin-3(2H)one. This compound has the chemical formula:

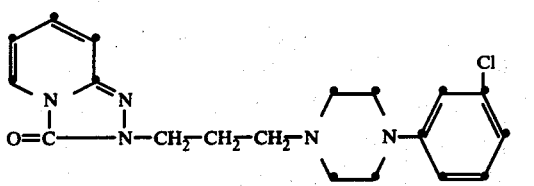

Trazodone is the subject of U.S. Pat. No. 3,381,009 and Japanese Pat. No. 555,140 in which the drug's pharmacological and therapeutic properties are attributed to its tranquilizing, hypotensive and analgesic actions.

A use Patent application (Ser. No. 608,690) has also been presented in the U.S. for the use of trazodone in acute vascular diseases, such as stroke.

Etoperidone is 3H-1,2,4-triazol-3-one-2[3-[4(m-chlorophenyl)-1-piperazinyl]-propyl]-4,5-diethyl-2,4-dihydro). This compound has the chemical formula:

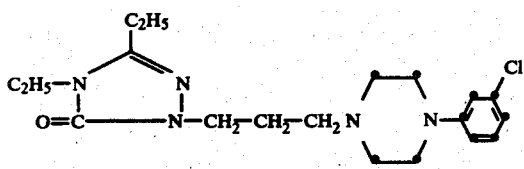

Etoperidone is the subject of U.S. Pat. No. 3,857,845 in which the drug's pharmacological and therapeutic properties are attributed to its tranquilizing, hypotensive and analgesic actions.

U.S. Pat. No. 3,857,845 is owned by the assignee of the present patent application. The drug etoperidone is presently being used in therapy as a psychotropic agent, the main field of application being primary or secondary depressive and anxious-depressive states.

PRIOR ART

The new therapeutic application which is the subject of the present invention concerns the anti-tremor activity of the two compounds in Parkinsonism and in other extrapyramidal syndromes. In this respect, it should be recalled that several neurological syndromes, e.g. Parkinson's disease, are characterized by both muscular hypertonia and tremors. Trazodone and etoperidone reduce the second of these two main components of the Parkinsonian syndrome. The anti-tremor activity of the above-mentioned compounds has been observed both in man and laboratory animals and represents an unexpected discovery. It is generally considered, in fact, that the neurological disturbances characterizing Parkinsonism are cause by an altered ratio of the neurotransmitters acetylcholine and dopamine in the basal ganglia, with cholinergic dominance. According to classical theory, an adrenolytic drug ought to worsen the Parkinsonian symptoms and not cure some of them. Consequently, therapy is based on the use of anticholinergic drugs or drugs which (with different mechanism of action) potentiate the activity of dopaminergic neurons, e.g. dopamine precursors and amantadine. This is known from the following four references:

1. R. S. Schwab, A. C. England, D. C. Poskanzor and R. R. Young—Amantadine in the treatment of Parkinson disease. J. Am. Med. Ass. 208: 1168 (1969).
2. H. L. Klawans—The pharmacology of parkinsonisms (a review). Dis. Nerv. Syst. 29: 805 (1968)
3. A. Mancinella, E. Bartolucci and P. De Candia—La malattia di Parkinson: considerazioni terapeutiche e riabilitative. Clin. Ter. 74:83 (1975).
4. R. M. Pinder—The pharmacotherapy of Parkinsonism. In: "Progress in Medicinal Chemistry". Ed. G. P. Ellis and G. B. West, Vol. 9, Part 2, pp. 191–274, Butterworth, London 1972.

My study of trazodone and etoperidone was based on a different hypothesis. In particular, although fully aware of the importance of cholinergic mediation in the genesis of tremors, I hypothesized that an adrenergic mediation is also of prime importance. Several clinical and experimental observations are in favor of this hypothesis. It is well-known clinically that dopaminergic or adrenergic compounds, such as 1-dopa and amantadine may produce tremors as side effects. Although these substances are certainly effective against rigidity, the above observations would indicate that tremors and rigidity have a different neurotransmitter basis.

As far as the experimental field is concerned, I have demonstrated that by using adrenergic substances, such as clonidine, it is possible to produce tremors in laboratory animals. Doses of clonidine producing evident tremors range from 10 to 15 mg/kg 5.c. Clonidine-induced tremors are inhibited by trazodone and etoperidone. In addition, I have shown that even tremors produced by tremorine having the formula:

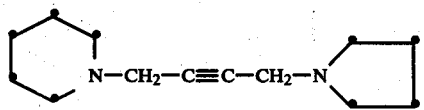

and oxotremorine, having the formula:

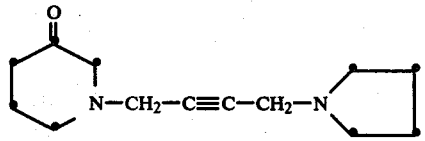

which are cholinergic agents, are also inhibited by trazodone and etoperidone.

A description of the method used and the results to study the anti-tremor activity in animals is as follows:

The experiments were conducted on CF$_1$ mice weighing 25 to 30 g. and on rabbits weighing 2 to 3 kg. Animals of both sexes were used and the results were pooled since no significant differences were observed between males and females.

The products were dissolved in physiological saline for the intravenous route and in distilled water for the other routes. All the doses reported refer to the salts.

Oxotremorine and clonidine were administered by the subcutaneous route at the doses of 1 and 12.5 mg./kg., respectively. Trazodone and etoperidone were administered by the intraperitoneal route. 30 Minutes prior to oxotremorine or clonidine.

The effects on the nicotine-induced tremor were studied by administering nicotine (1 mg./kg.) and trazodone or etoperidone by the intravenous route; the antagonist was injected 5 minutes before nicotine.

The investigators recording the effects of the drugs were not aware of the treatments being used. For the statistical evaluation of the results, Student's "t" test was used.

To record oxotremorine-induced tremors, a slightly modified version of the method of Everett[21] was used. Groups of 3 mice were injected with 1/mg.kg. of oxotremorine subcutaneously and placed in Perspex cages (15×39×25 cm.). The animals had no access to either food or water during the experiment. Each mouse was observed for the presence of tremor at 10-minute intervals for 60 minutes.

Tremor was assessed according to the scoring system described in Table I.

Table I

| Score | Tremor | Salivation | Piloerection |
|---|---|---|---|
| 0 | absent | absent | absent |
| 1 | mild | saliva between the teeth | head and neck |
| 2 | moderate | saliva around the mouth | head, neck and scapular region |
| 3 | marked | saliva up to the ears | as above plus mid-dorsal region |
| 4 | very severe | saliva even on the animal's back | total |

Clonidine-induced tremors were studied as follows:

Groups of 3 mice were injected with 12.5 mg./kg./ of clonidine and then placed in Perspex cages (15×29×24 cm.). During the experiment the animals had no access to either food or water. Each mouse was observed for the presence of tremor for 60 minutes. The observations were made at 5-minute intervals for the first 30 minutes and at 10-minute intervals thereafter. Tremors and piloerection were assessed with the scoring system described in Table I.

Nicotine-Induced Tremor was studied as follows:

Groups of 4 rabbits were used for each experiment. Tremor was assessed as described by Bovet and Longo.

RESULTS

Oxotremorine-Induced Tremor and Salivation

Table II summarizes the effects of the drugs under study on oxotremorine-induced tremor and salivation.

Apart from pyrilamine, PCPA and 5-HTP, all the drugs studied inhibited oxotremorine-induced tremor. Salivation, on the other hand, was inhibited only by atropine and imipramine, two drugs with definite anticholinergic properties. It should be noted, however, that the lower dose of imipramine inhibited only tremor whereas the higher dose inhibited both tremor and salivation, its effect on tremor being still more marked.

Table II

Effects of some drugs on oxotremorine-induced tremor and salivation

| Drugs | Doses in mg./kg. i.p. | No. Mice | Percent Change with Respect to Controls | |
|---|---|---|---|---|
| | | | Tremor | Salivation |
| atropine | 0.4 | 12 | $-30^{(1)}$ | $-42^{(3)}$ |
| | 0.8 | 12 | $-73^{(3)}$ | $-87^{(3)}$ |
| pyrilamine | 12.5 | 12 | 0 | +6 |
| dibenzyline | 6.2 | 12 | $-14$ | $-5$ |
| | 12.5 | 12 | $-46^{(3)}$ | $-12$ |
| PCPA | 150 | 12 | $-2$ | $+11$ |
| 5-HTP | 100 | 12 | $-12$ | 0 |
| imipramine | 12.5 | 12 | $-52^{(3)}$ | $-10$ |
| | 25 | 12 | $-93^{(3)}$ | $-20^{(1)}$ |
| trazodone | 12.5 | 12 | $-36^{(2)}$ | 0 |
| | 25 | 12 | $-87^{(3)}$ | $-10$ |
| etoperidone | 12.5 | 12 | $-29^{(1)}$ | |
| | 25 | 12 | $-81^{(3)}$ | |

Clonidine-Induced Tremor and Piloerection

The effects of the drugs under study on clonidine-induced tremor and piloerection are reported in Table III.

Tremor and piloerection were inhibited by dibenzyline, trazodone, and etoperidone. These drugs had a greater inhibiting effect on piloerection than on tremor at both dose levels. On the other hand, at the higher doses used, both atropine and imipramine potentiated tremor without affecting piloerection.

Pyrilamine, PCPA and 5-HTP had no effect on either tremor or piloerection.

Table III

Effects of some drugs on clonidine-induced tremor and piloerection

| Drugs | Doses in mg./kg. i.p. | No. Mice | Percent Change With Respect to Controls | |
|---|---|---|---|---|
| | | | Tremor | Piloerection |
| atropine | 0.4 | 6 | +5 | 0 |
| | 0.8 | 8 | $+19^{(1)}$ | +7 |
| pyrilamine | 12.5 | 6 | +5 | 0 |
| dibenzyline | 6.2 | 8 | $-7$ | $-48^{(4)}$ |
| | 12.5 | 8 | $-37^{(4)}$ | $-75^{(4)}$ |
| PCPA | 150 | 6 | +5 | $-7$ |
| 5-HTP | 100 | 6 | 0 | $-8$ |
| imipramine | 12.5 | 8 | +13 | 0 |
| | 25 | 8 | $+18^{(2)}$ | $-6$ |
| trazodone | 12.5 | 8 | $-22^{(1)}$ | $-31^{(3)}$ |
| | 25 | 8 | $-38^{(4)}$ | $-53^{(4)}$ |
| etoperidone | 12.5 | 8 | $-17^{(1)}$ | |
| | 25 | 8 | $-24^{(3)}$ | |

(1),(2),(3) and (4) significantly different from controls at $p<0.05$; $<0.02$; $<0.01$ and $<0.001$, respectively.

Nicotine-Induced Tremor

Trazodone and etoperidone inhibited nicotine-induced tremor; the lowest effective doses were 5 and 2.5 m.g./k.g. respectively.

Since trazodone and etoperidone are devoid of antichlolinergic effects, but on the contrary have a potent adrenolytic action, their anti-tremor activity is attributed to their adrenolytic properties.

Trazodone and etoperidone are adrenolytic agents. This has been reported in a paper on trazodone which has already been published [Silvestrini, B. et al. Int. J. Neuropharniacol. 1968, 7, 587–599] and in another report on etoperidone which is soon to be published ["Pharmacological investigation on Etoperidone, A new psychotropic agent" by Lisciani, R-Baldini, A.—De Feo, G. and Silvestrini, B.]

Numerous clinical trials with experiments trazodone and etoperidone used in depressions and other mental diseases in humans have demonstrated that they are well tolerated. A study with these drugs was consequently started in extra-pyramidal syndromes characterized by tremors. The trazodone and etoperidone dosage was a 50 mg. capsule 3 times daily after meals. This was also the appropriate daily dosage for treating the accompanying psychopathological state present in all the patients. The diagnosis of Parkinson's disease was made according to the common medical criterion found in medical books. The patients did not receive any other therapy while trazodone and etoperidone were being tested. The effects of the drugs on tremor were assessed as follows:

graphic recording of tremor by means of accelerometer.
    daily clinical observation
    design tracing test
    handwriting test The registration of tremor was made with a piezoelectric accelerometer attached to the index finger of the more affected hand. After amplification the signal was transmitted to the recording system of a polygraph together with the ECG.

The patient was put in an acoustically isolated room; the arm was put in a standard position so as to allow the evaluation of any changes in tremor and eliminate any artifacts.

This technique is particularly suitable for the evaluation of the immediate effect of the drugs. In this case the times of recording consisted of a basal period of 10 minutes and subsequent periods of 3 minutes each at 10-36-60 minutes from the administration. An evaluation of the tracings was made by calculating the average amplitude of intervals of 1 minute. The amplitude at times 10-36-60 minutes were compared with those under basal conditions calculating the significance with the Student's "t" test.

Clinical observation and the handwriting and tracing tests were more suitable for the evaluation of the effect of the drug after repeated administrations. In this case, tests were performed before the administration of the drug, after 1 week, 2 weeks and 4 weeks of treatment.

Tremor was scored as follows:
    worsening=3, unchanged=2, improvement=1, disappearance of tremor=0

The data collected with this method in two groups of patients, one group treated with the product and another with placebo, were statistically analyzed by means of the Student's "t" test and/or the Pearson's $X^2$ test.

The therapeutic results obtained were favorable and are summarized below.

A clinical trial was done in —patients suffering of Parkinson with tremors. The duration of the treatment was 10 days. In 10 over 13 patients the therapeutic results were good with an almost complete disappearance of tremors. In 2 cases therapeutic effects were mild and in 1 case the trazodone had practically no effect. Even if the study was done in a small number of patients, results obtained were so good as to support the conclusions that trazodone is an elective drug for treating Parkinsonian tremors. Etoperidone was studied as follows:

a double blind placebo controlled cross-over clinical trial was performed on a group of 10 patients (7 males and 3 females) suffering from Parkinsonism and ranging in age from 60 to 72 years (average age: 64). The order in which the products (etoperidone and placebo) were given was established by randomization. The duration of treatment for each product was two weeks. The placebo was supplied in identical capsules and at the same dosage to the drug under study. A careful clinical examination was performed each day and the improvement in the neurological symptomatology was assessed at the end of treatment according to the following scale: "nil - slight - moderate - good".

In 9 out of 10 patients there was an improvement during etoperidone period in "tremor" and in any other type of abnormal spontaneous movement which may have been present (oculogyric crisis, movement of the head, etc.). The improvement was observed from the 4th-5th day and, at the end of treatment, the overall clinical assessment was "moderate" in 5 cases and "good" in 4 cases. On the other hand, there was no therapeutic activity on rigidity and akinesia which are instead known to respond well to the traditional anti-Parkinsonian drugs.

In 4 out of 10 patents there was an improvement during placebo period ("slight" in 1 case, "moderate" in 3 cases). The following Table IV summarizes and analyzes statistically the results keeping in mind that we are dealing with related samples.

TABLE IV

| PLACEBO | ETOPERIDONE | | |
|---|---|---|---|
| | moderate or good | nil or slight | moderate or good |
| | | 0 | 3 |
| nil or slight | | 1 | 6 |

Mc Nemar Test
P (one tailed) = 0.016

Etoperidone was studied in doses ranging from 25 up to 100 mg. three times a day orally. The dose of 50 mg. was found to be the most convenient one. The drug was preferably administered after meals. The general knowledge of the pharmaco-kinetics of the drug and the knowledge on the equivalence between the different ways of administration strongly indicate that the anti-tremor activity may be obtained by the subcutaneous or intramuscular injection of 25-50 mg.

The mean body weight of the patients was around 70 kg. Therefore the effective dose of the drug is in the range of 0.7 mg/kg three times a day orally.

As far as the dose is concerned, it should be noted that the doses effective against tremor correspond to the low-average doses used in the therapy of mental conditions. In this connection it should be stressed that etoperidone was originally developed as a psychotherapeutic agent with anti-depressant activities and that the doses ranged between 25-50 mg three times a day orally in mild conditions and up to 100-150 mg three times a day orally in the more severe cases of depression.

In conclusion, the observations and the studies described here provide evidence that trazodone and etoperidone are capable of inhibiting extrapyramidal tremors. This discovery was not foreseen either on the basis of the general knowledge available on the subject (it has in fact been thought so far that an anti-Parkinson action could be obtained with anti-cholinergic or adrenergic drugs, but not with adrenolytic drugs such as trazodone and etoperidone) or on the basis of the previous uses of etoperidone.

I claim:

1. A process for the treatment of tremors in Parkinsonism and in other extrapyramidal syndromes which comprises administering orally to a human afflicted with Parkinsonism an amount of trazodone of the formula

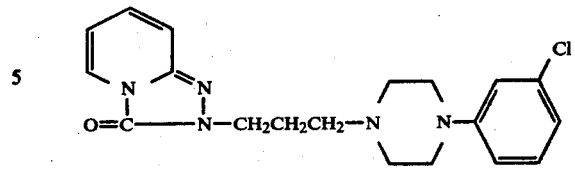

or of etoperidone of the formula:

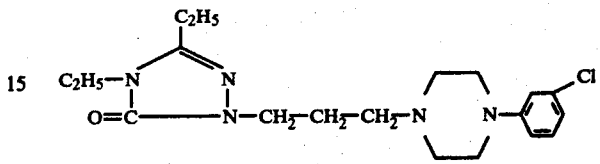

in the range of about 25 mg. three times a day.

2. A process according to claim 1, wherein the etoperidone is administered orally.

* * * * *